US010311568B2

United States Patent
Omi (10) Patent No.: US 10,311,568 B2
(45) Date of Patent: Jun. 4, 2019

(54) IMAGE PROCESSING APPARATUS, CONTROL METHOD THEREOF, AND COMPUTER-READABLE STORAGE MEDIUM

(71) Applicant: CANON KABUSHIKI KAISHA, Tokyo (JP)

(72) Inventor: Hiroyuki Omi, Kamakura (JP)

(73) Assignee: Canon Kabushiki Kaisha, Tokyo (JP)

( * ) Notice: Subject to any disclaimer, the term of this patent is extended or adjusted under 35 U.S.C. 154(b) by 164 days.

(21) Appl. No.: 15/283,850

(22) Filed: Oct. 3, 2016

(65) Prior Publication Data

US 2017/0103522 A1 Apr. 13, 2017

(30) Foreign Application Priority Data

Oct. 8, 2015 (JP) ................................ 2015-200473

(51) Int. Cl.
*G06K 9/00* (2006.01)
*G06T 7/00* (2017.01)
*G06T 5/00* (2006.01)
(Continued)

(52) U.S. Cl.
CPC .......... *G06T 7/0012* (2013.01); *A61B 6/5205* (2013.01); *A61B 6/5264* (2013.01); *G06T 5/003* (2013.01); *G06T 7/20* (2013.01); *G06T 7/246* (2017.01); *G06T 7/73* (2017.01); *G06T 2207/10072* (2013.01); *G06T 2207/10116* (2013.01); *G06T 2207/20021* (2013.01);
(Continued)

(58) Field of Classification Search
CPC ..... G06T 7/246; G06T 11/003; G06T 11/006; G06T 2207/10016; G06T 2207/10116; G06T 2207/20016; G06T 2207/20201; G06T 2207/30012; G06T 2207/30168; G06T 2207/30196; G06T 2207/30201; G06T 2211/424; G06T 7/0002; A61B 6/032; A61B 6/5205; A61B 6/5264
See application file for complete search history.

(56) References Cited

U.S. PATENT DOCUMENTS 5,015,853 A 5/1991 Nakajima
8,705,172 B2* 4/2014 Kleppe .............. G02B 21/0036
359/385

(Continued)

FOREIGN PATENT DOCUMENTS

JP S63-133760 A 6/1988
JP 2013-102850 A 5/2013
JP 2014-079558 A 5/2014

OTHER PUBLICATIONS

Deshpande Ashwini M et al: "A Spatially Variant Motion Blur Removal Technique for Single Image Deblurring", 2014 Annual IEEE India Conference (INDICON), IEEE, Dec. 11, 2014, pp. 1-6, India.

(Continued)

*Primary Examiner* — Avinash Yentrapati
(74) *Attorney, Agent, or Firm* — Venable LLP (57) ABSTRACT

An image processing apparatus includes an image acquisition unit adapted to acquire a radiation image capturing an object, a function acquisition unit adapted to acquire a point spread function from the radiation image, and a determination unit adapted to determine, based on a state of the point spread function, presence/absence of a movement of the object in the radiation image.

12 Claims, 9 Drawing Sheets

(51) Int. Cl.
  *G06T 7/20* (2017.01)
  *A61B 6/00* (2006.01)
  *G06T 7/73* (2017.01)
  *G06T 7/246* (2017.01)

(52) U.S. Cl.
  CPC .............. *G06T 2207/20068* (2013.01); *G06T 2207/20201* (2013.01); *G06T 2207/30061* (2013.01); *G06T 2207/30168* (2013.01)

(56) References Cited

U.S. PATENT DOCUMENTS

| | | | |
|---|---|---|---|
| 9,117,289 B2 | 8/2015 | Matsumoto | |
| 9,147,267 B2* | 9/2015 | Bruder | G06T 11/003 |
| 9,619,893 B2* | 4/2017 | Kawamura | A61B 6/5264 |
| 2005/0047672 A1* | 3/2005 | Ben-Ezra | H04N 5/2258 |
| | | | 382/255 |
| 2007/0258707 A1* | 11/2007 | Raskar | G03B 17/00 |
| | | | 396/52 |
| 2009/0041305 A1* | 2/2009 | Luo | G06T 7/0002 |
| | | | 382/107 |
| 2010/0231732 A1* | 9/2010 | Baxansky | G06T 5/003 |
| | | | 348/208.4 |
| 2011/0090345 A1* | 4/2011 | Ishii | H04N 5/23248 |
| | | | 348/169 |
| 2011/0199492 A1* | 8/2011 | Kauker | G06T 5/003 |
| | | | 348/208.1 |
| 2012/0050755 A1* | 3/2012 | Chandu | H04N 1/6033 |
| | | | 358/1.9 |
| 2013/0121556 A1* | 5/2013 | Matsumoto | A61B 6/50 |
| | | | 382/132 |
| 2015/0193948 A1 | 7/2015 | Kawamura | |
| 2015/0379726 A1 | 12/2015 | Kawamura | |

OTHER PUBLICATIONS

Tico M et al: "Motion Blur Identification Based on Differently Exposed Images", 2006 International Conference on Image Processing, Oct. 8, 1996, pp. 2021-2024, USA.

Anonymous: "Blind Deconvolution", Wikipedia, Apr. 6, 2013, (Retrieved from the Internet: URL:https://en.wikipedia.org/w/index.php?title=Blind_deconvolution&oldid=549046430).

* cited by examiner

PSF WITHOUT MOVEMENT

FIG. 5B

PSF WITH MOVEMENT

IMAGE PROCESSING APPARATUS, CONTROL METHOD THEREOF, AND COMPUTER-READABLE STORAGE MEDIUM

BACKGROUND OF THE INVENTION

Field of the Invention

The present invention relates to an image processing apparatus, a control method thereof, and a computer-readable storage medium and, more particularly, to a technique of detecting the presence/absence of a movement of an object in a radiation image.

Description of the Related Art

When a radiation image such as an X-ray image is acquired, the image quality of an image may degrade for various reasons. One of the reasons is movement. The movement is a movement of an object during imaging and tends to occur in imaging that puts a burden on a patient such as imaging with a long irradiation time or imaging which requires the patient to hold his/her breath. When a movement occurs, a blur occurs in the acquired image, and the image quality is degraded. A technician who performed the imaging checks whether a movement has occurred by observing the acquired radiation image on a monitor. If a movement has occurred, re-imaging is necessary since the image is not suitable for diagnosis.

However, the monitor used by the technician to check for a movement is often a monitor with low resolution that is just enough to check whether a part necessary for diagnosis has been captured or whether the imaging dose is appropriate. Hence, in order to check for a movement, the entire image needs to be observed by enlarging the image. If such checking occurs each time imaging is performed, not only will it reduce the work efficiency of the technician but it may also cause the technician to miss a movement.

Movement detection by automatically determining whether a movement has occurred in the acquired radiation image is known. As a procedure of detecting movement, Japanese Patent Laid-Open No. 2014-079558 discloses a method of detecting a movement by detecting an edge included in the image and obtaining the high frequency component and low frequency component, based on a feature in which a high frequency component is degraded while a low frequency component is not. On the other hand, Japanese Patent Laid-Open No. 2013-102850 discloses a method of detecting a movement by obtaining a spatial frequency response in the lung fields, based on a feature in which a response in a specific frequency range is attenuated.

However, since the arrangement of Japanese Patent Laid-Open No. 2014-079558 detects the movement by an edge, a movement in which the edge such as a bone does not blur is difficult to detect. For example, since the lung fields move but the ribs barely move, it is difficult to detect a movement that has occurred due to a failure to hold the breath. On the other hand, since the arrangement Japanese Patent Laid-Open No. 2013-102850 detects the movement based on the degradation of a specific frequency range response, it is difficult to distinguish whether the degradation is due to a movement or a structural cause, and the detection accuracy is problematically reduced.

SUMMARY OF THE INVENTION

The present invention provides a technique of detecting, with higher accuracy, image quality degradation due to movement.

According to one aspect of the present invention, an image processing apparatus includes: an image acquisition unit adapted to acquire a radiation image capturing an object; a function acquisition unit adapted to acquire a point spread function from the radiation image; and a determination unit adapted to determine, based on a state of the point spread function, presence/absence of a movement of the object in the radiation image.

According to another aspect of the present invention, a control method of an image processing apparatus, includes: acquiring, by an image acquisition unit, a radiation image capturing an object; acquiring, by a function acquisition unit, a point spread function from the radiation image; and determining, by a determination unit, based on a state of the point spread function, presence/absence of a movement of the object in the radiation image.

Further features of the present invention will become apparent from the following description of exemplary embodiments (with reference to the attached drawings).

DESCRIPTION OF THE EMBODIMENTS

Embodiments of the present invention will be described in detail below with reference to the accompanying drawings.

(Arrangement of Image Processing Apparatus)

Figure 1:
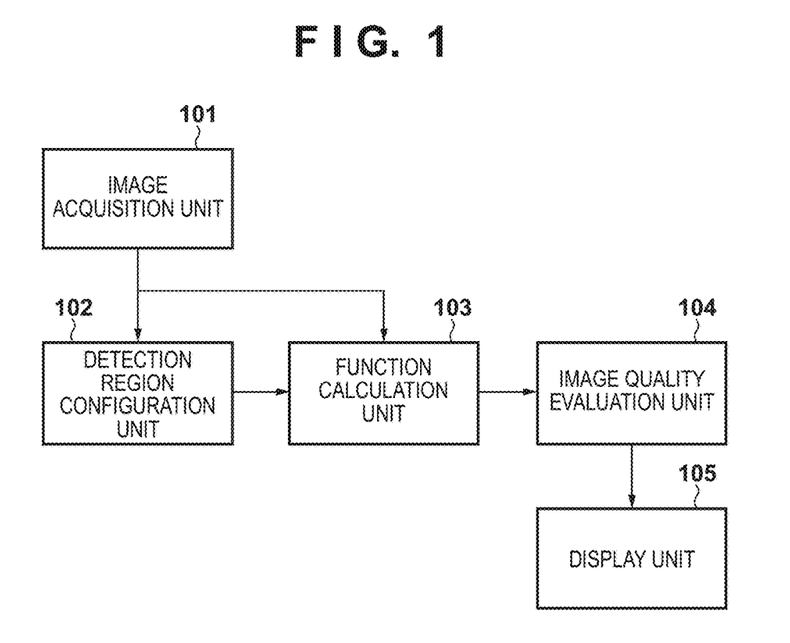
FIG. 1 is a block diagram showing an example of the functional arrangement of an X-ray image processing apparatus.

In this embodiment, image quality degradation due to a movement is associated with an optical image degradation to calculate a filter (Point Spread Function=PSF) that is causing the degradation, and the occurrence of the movement is detected from the state of the PSF (for example, the shape of the PSF). The arrangement of an X-ray image processing apparatus as an image processing apparatus according to the first embodiment of the present invention will be described with reference to FIG. 1. FIG. 1 is a block diagram showing an example of the functional arrangement of the X-ray image processing apparatus.

The X-ray image processing apparatus according to the first embodiment includes an image acquisition unit 101, a detection region configuration unit 102, a function calculation unit 103, an image quality evaluation unit 104, and a display unit 105. The image acquisition unit 101 receives an X-ray image acquired by an X-ray sensor, generates an image (to be referred to as a "pre-processed image" hereinafter) by performing predetermined pre-processing, and outputs the pre-processed image. Although an example using an X-ray image as a processing target will be described in this embodiment, another medical image such as a radiation image acquired by radiation other than X-rays may be a target.

The detection region configuration unit 102 receives a pre-processed image, determines a detection region to calculate a point spread function (to be referred to as "PSF" hereinafter), and outputs the result. The function calculation unit 103 receives the pre-processed image and the detection region, calculates a PSF from the pre-processed image in the detection region, and outputs the PSF. The image quality evaluation unit 104 receives the PSF, evaluates whether a movement has occurred by analyzing the PSF, and outputs the evaluation result. The display unit 105 receives the evaluation result calculated by the image quality evaluation unit 104, outputs the evaluation result to a display device such as a monitor, and causes the display device to display the evaluation result.

Figure 2:
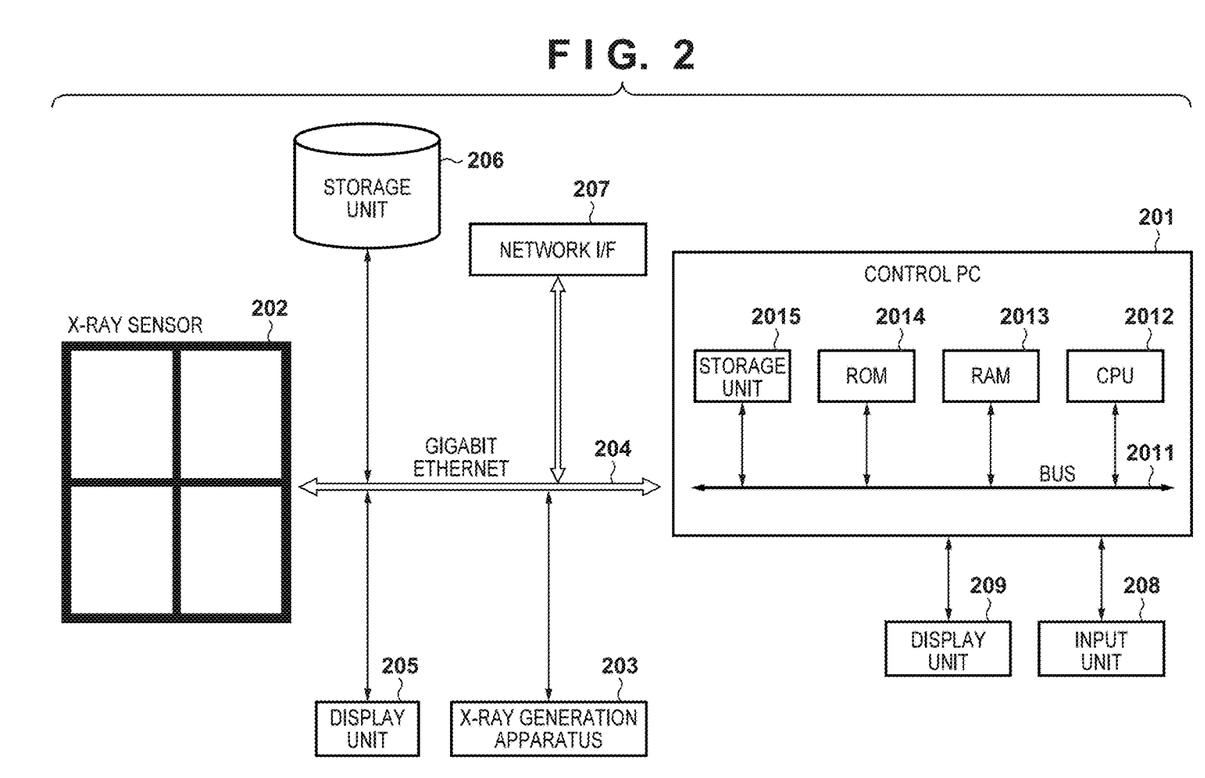
FIG. 2 is a block diagram showing an example of the hardware arrangement of the X-ray image processing apparatus.

If the arrangement shown in FIG. 1 is implemented by using a PC (personal computer), it becomes like the arrangement shown in FIG. 2. FIG. 2 is a block diagram showing an example of the hardware arrangement of an X-ray image processing apparatus.

In FIG. 2, a control PC 201, an X-ray sensor 202, and an X-ray generation apparatus 203 are connected via a GigaBit Ethernet 204. The signal line connecting the control PC 201, the X-ray sensor 202, and the like need not be a GigaBit Ethernet and may be any wired or wireless medium as long as it can transmit information. For example, the signal line may be a CAN (Controller Area Network), an optical fiber, a wireless LAN, or the like.

Furthermore, a display unit 205, a storage unit 206, a network interface (I/F) 207 are connected to the GigaBit Ethernet 204. The control PC 201 has, for example, an arrangement in which a CPU (Central Processing Unit) 2012, a RAM (Random Access Memory) 2013, a ROM (Read Only Memory) 2014, and a storage unit (storage device) 2015 are connected to a bus 2011. RAM is an abbreviation of Random Access Memory, and ROM is an abbreviation of Read Only Memory.

An input unit 208 is connected to the control PC 201 by an interface such as a USB or PS/2, and a display unit 209 is connected to the control PC 201 by an interface such as a VGA or DVI. A command is transmitted to the X-ray sensor 202 and the display unit 205 via this control PC 201. In the control PC 201, processing contents for each imaging mode are stored in the storage unit 2015 that serves as a software module, loaded in the RAM 2013 in accordance with a designation instruction from a designation device (a keyboard, a pointing device, or the like) (not shown), and executed.

In the first embodiment, an example in which the functional units 101 to 104 in the arrangement shown in FIG. 1 are stored in the storage unit 2015 as software modules (computer programs) will be described. All or some of the functional units 101 to 104 shown in FIG. 1 may be implemented as a dedicated image processing board as a matter of course. The implementation can be selected in accordance with the usage or the purpose. The display unit 105 shown in FIG. 1 can be formed by, for example, the display unit 205 via the GigaBit Ethernet 204 or the display unit 209 connected to the control PC.

Operations of the detection region configuration unit 102, the function calculation unit 103, and the image quality evaluation unit 104 in the X-ray image processing apparatus including an arrangement as described above will be described in detail below.

(Processing Procedure)

Figure 3:
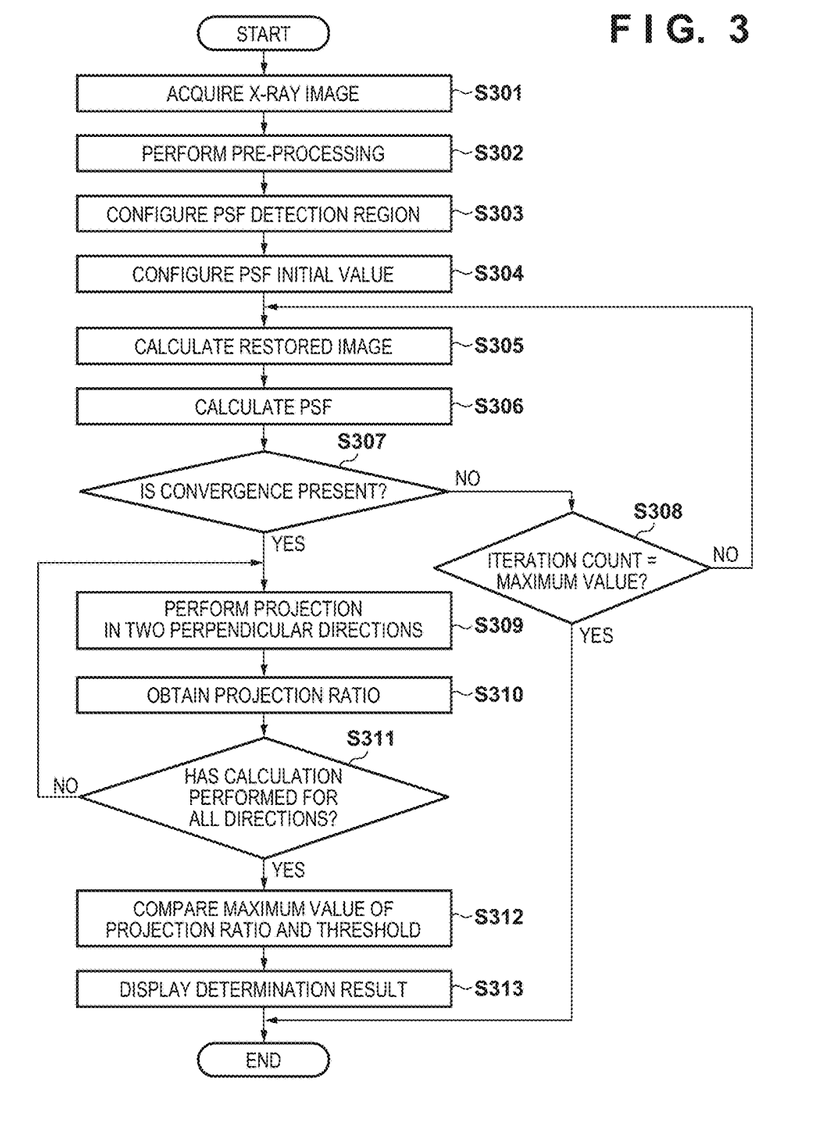
FIG. 3 is a flowchart showing a processing procedure of movement detection processing.

Processing executed by the X-ray image processing apparatus will be described next with reference to FIGS. 1 and 3. FIG. 3 is a flowchart showing the procedure of processing executed by the X-ray image processing apparatus. Each step to be described below is executed by the CPU 2012 which controls the entire apparatus based on a computer program.

In step S301, the image acquisition unit 101 acquires an image by the X-ray sensor and performs pre-processing to the acquired image in step S302. The pre-processing is processing of correcting the characteristics of the sensor such as offset correction, gain correction, or defect correction, and processing of setting a state in which the correlation with peripheral pixels is maintained. A movement can be detected more accurately by removing a structure such as a grid that is unrelated to the movement at the stage of the pre-processing.

Next, the detection region configuration unit 102 configures a region to calculate a PSF (step S303). The location where the movement has occurred may not be the entire image. For example, in a region (to be referred to as a "direct ray region" hereinafter) where the X-rays directly enter the sensor without passing through an object (a human body or the like), blurring does not occur since nothing will change even if the object moves. Even inside the object, for example, in a case of a movement from a failure to hold the breath or the like, the entire image does not blur but only the lung fields blur. Hence, rather than calculating a single PSF from the entire image, it is preferable to configure a plurality of calculation regions from the image and calculate a PSF for each configured region. Additionally, a movement can be grasped locally by decreasing the size of a region to be configured. If a movement is seen as an entire image, the movement becomes complex since various kinds of movements are added, and the PSF to be calculated becomes a complex shape. However, if the movement is seen locally, the movement can be seen as a one directional movement, and the PSF to be calculated becomes a simple shape. Therefore, the detection accuracy of a movement can be increased by making the PSF have a simple shape.

Figure 4A:
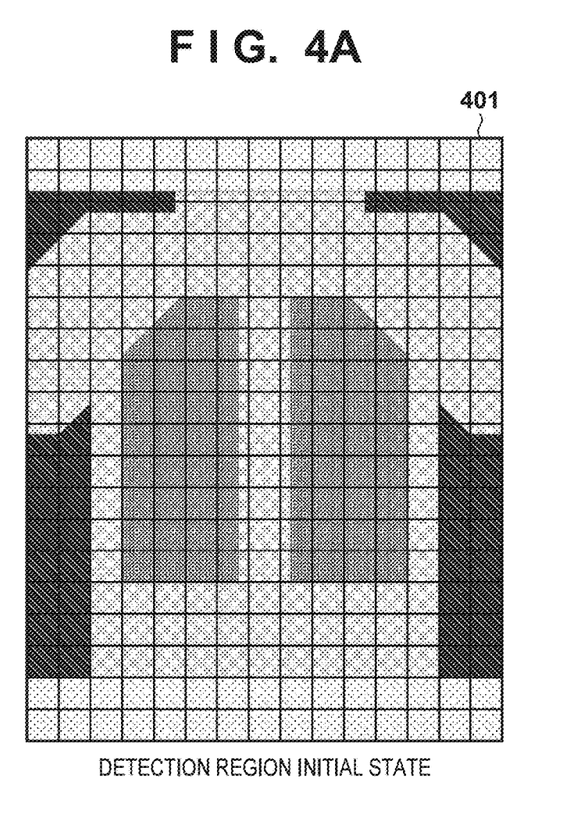
FIGS. 4A and 4B are views each showing detection region configurations.
Figure 4B:
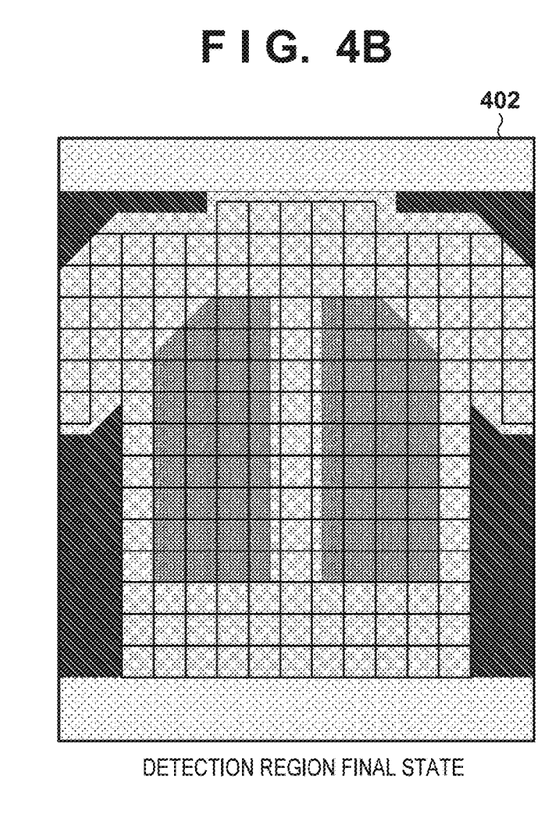

As the configuration method of a detection region, for example, an entire image is divided into fixed-size blocks as shown in 401 of FIG. 4A. Then, blocks having areas occupied by a collimation region or the direct ray region are excluded. 402 of FIG. 4B shows an example of blocks selected by excluding such regions.

The collimation region and the direct ray region can be extracted using any kind of method. For example, Japanese Patent Laid-Open No. 63-133760 describes a method in which a region having added/totaled data of image information of a radiation image which is equal to or more than a threshold is extracted as a collimation region. This method configures X- and Y-axes along two adjacent sides of the outline of a rectangular exposure field and adds and totals image data in the configured X-axis direction and Y-axis direction. The value of the added/totaled data within the exposure field is higher than that of a region, outside the exposure field, which is hardly irradiated with X-rays. Consequently, this method calculates a position on the Y-axis at which the value of the added/totaled data in the X-axis direction is equal to or higher than a predetermined threshold TH and a position on the X-axis at which the value of the added/totaled data in the Y-axis direction is equal to or higher than the predetermined threshold TH. Then, a rectangular region surrounded by a straight line in the X-axis direction on the calculated position on the Y-axis and a straight line in the Y-axis direction at the calculated position on the X-axis is configured as a collimation region.

The method of extracting a direct ray region (direct irradiated region) is based on a fact that if, for example, an image histogram is calculated, the direct irradiated region concentrates in a high-pixel value region. Therefore, it is possible to extract the direct irradiated region by eliminating several % from the high-pixel value side of the histogram range. Each block selected by excluding the collimation region and the direct ray region, which are extracted in this manner, from the entire image is configured as the detection region to calculate the PSF.

Next, the function calculation unit 103 calculates the PSF. In general, if a point image is input to an imaging apparatus, a blurred image will be captured. A PSF (point spread function) is a function expressing the characteristics of the imaging apparatus when various kinds of image degradation that accompany an imaging operation are associated with the characteristics of the imaging apparatus which outputs a blurred image when such a point image is input. The PSF calculation method uses an image restoration method. Image restoration is a generic name for image processing, such as noise removal, blur removal, and super-resolution, to restore an original image from a degraded image. The mathematical expression of image degradation is $$y = DHx + n \tag{1}$$

where y represents a degraded image (corresponding to the radiation image), x represents an original image, and the remaining terms represent respective parameters expressing the causes of degradation. D represents a matrix expressing down sampling, H represents a matrix expressing a blur, and n represents a matrix expressing noise. The PSF calculated by the function calculation unit 103 corresponds to the matrix H.

This embodiment provides a technique of detecting movement. Hence, the matrix D and the matrix n are ignored and a simple equation (2) is used.

$$y = Hx \tag{2}$$

Although equation (2) is a simple linear model, since the original image x and the matrix H are both unknown variables, a solution cannot be uniquely obtained. Hence, Hx as an approximate solution of the degraded image y is calculated upon regularization. The MAP (Maximum a Posteriori) method is a calculation method of an approximate solution. The MAP method is a stochastic method that maximizes the posterior probability in consideration of prior probability as a priori information. Other than the MAP method, there is also the IBP (Iterative Back Projection) method used in CT (Computed Tomography) and the like. In these methods, a series of processes in which an estimated image and PSF are newly generated based on a predetermined estimated image (restored image), a PSF, and an observed image (radiation image), and
an estimated image and a PSF are further generated based on this new estimated image, the new PSF, and the observed image are repeated until an error of the estimated image and the observed image becomes less than a predetermined value. Since a state in which the error of the estimated image and the observed image becomes less than the predetermined value is a state in which the observed image has been sufficiently approximated by the estimated image, it is possible to assume that the PSF at this time sufficiently expresses the image degradation characteristics. Hence, the function calculation unit 103 acquires the PSF obtained when the error of the estimated image and the observed image becomes less than the predetermined value as the PSF that sufficiently expresses the image degradation characteristic. Note that the predetermined estimated image configured first is the image serving as the initial value for applying iterative processing of extracting the estimated image (restored image). The predetermined estimated image can be, for example, an image having uniform pixel values or an image based on the observed image.

In this manner, the function calculation unit 103 repeats processing in which (a) based on a first restored image (estimated image) of a radiation image, a first point spread function (first PSF), and the radiation image (observed image), a second restored image is acquired as a updated first restored image and (b) based on the second restored image, the first point spread function (first PSF), and the radiation image (observed image), a second point spread function (second PSF) is acquired as the updated first point spread function (first PSF). This processing is repeated until a difference between the radiation image and an image acquired by applying the second point spread function (second PSF) to the second restored image becomes less than a predetermined value, and the point spread function (PSF) is acquired from the radiation image.

There is a method of reconstructing a CT image by using the IBP method. There is also a method of using a cepstrum as a method of calculating from a frequency space. The cepstrum is acquired by further performing a Fourier transform on a Fourier-transformed image, and the PSF is calculated from its feature.

Any method may be used to calculate the PSF, but a case in which the IBP method is used to calculate the PSF will be described in this embodiment. First, the function calculation unit 103 configures an initial value of the PSF (step S304). The input initial value can be, for example, an image in which all elements have been normalized by the same value. The PSF size is decided by the amount of a detected movement. For example, a 0.2-mm blur occurs when an average of the movements of two pixels is taken from a 0.2-mm resolution image (PSF size is 2 pixels). Hence, in order to detect a 1-mm blur, an average of the movements of 1 mm/0.2 mm+1=6 pixels is necessary, and 6 pixels are needed as the PSF size.

Next, the restored image is calculated from the PSF configured with the initial value and the observed image (step S305) by $$x_j^{(k+1)} = x_j^{(k)} + \alpha \sum_i \left( \gamma_x \cdot y_i - \sum_j h_{ji} x_i^{(k)} \right) h_{ij} - \alpha \cdot g(x) \tag{3}$$

where h represents a PSF element, $\alpha$ and $\gamma_x$ represent terms for adjusting convergence, and g represents a regularization term. k represents an iteration count expressing an iterative count of the processes in steps S305 and S306, and k=0 when the process of step S305 is first performed. i and j represent the image and PSF positions. $x^{(k)}$ represents a pixel value of the restored image when k is the iteration count. $x^{(0)}$, that is, the initial value of the restored image is predetermined and, for example, $x^{(0)}$ can be the same as the pixel value y of the observed image.

h is updated for each PSF calculation in step S306, and $h^{(k)}$ represents h after a kth PSF calculation has been performed. $h^{(0)}$ is the initial value configured in step S304, and $\alpha$, $\gamma_x$, and g are predetermined.

Next, a new PSF is calculated (step S306) from the observed image and the restored image acquired by equation (3) by $$h_j^{(k+1)} = h_j^{(k)} + \beta \sum_i \left( \gamma_h \cdot y_i - \sum_j x_{ji} h_i^{(k)} \right) x_{ij} - \beta \cdot \gamma_h \cdot h_j^{(k)} \quad (4)$$

where $\beta$ and $\gamma_h$ represent terms for adjusting convergence. $\beta$ and $\gamma_h$ are predetermined.

Next, whether convergence is present in the restored image and the PSF acquired here is evaluated (step S307) by $$\|y - Hx\|^2 < th1 \quad (5)$$

if the error expressed by the left-hand side of the expression (5) is within the range of the predetermined threshold th1, it is determined that convergence is present (YES in step S307), and the process advances to step S309 upon ending the PSF calculation. Otherwise, if the absence of convergence is determined (NO in step S307), and the process advances to step S308.

It is determined in step S308 whether the number of times (iteration count k) the absence of convergence has been determined in step S307 exceeds the preconfigured maximum iteration count. The processing ends if the count has been exceeded (YES in step S308). Otherwise (NO in step S308), the iteration count k is incremented by 1 (k=k+1), and the process returns to step S305 to calculate the restored image, and the processing is repeated. In this manner, letting the maximum iteration count be the upper limit, the PSF calculation is repeated until the error converges within the specific range th1. If the error does not converge, the processing is ended (step S308) since the PSF cannot be accurately obtained. Note that a result acquired from performing processing using a fixed iteration count can be output without performing the error evaluation in step S307. In this case, upon reaching the maximum iteration count in step S308, the processing is not ended, but step S309 and subsequent steps are performed.

In this manner, in steps S305 to S308, processes in which
the second restored image as the updated first restored image is acquired based on the first restored image of the radiation image, the first PSF (point spread function), and the radiation image, and
the second PSF as the updated first PSF is acquired based on the second restored image, the first PSF, and the radiation image
are repeated until the difference between the radiation image and the image acquired by applying the second PSF to the second restored image is less than a predetermined value, and the PSF is acquired from the radiation image.

Figure 5A:
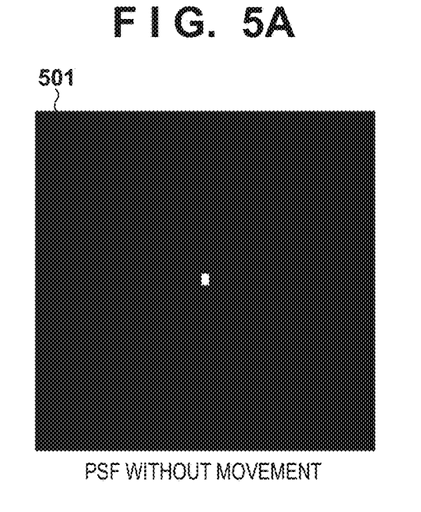
FIGS. 5A and 5B are views showing examples of PSF.
Figure 5B:
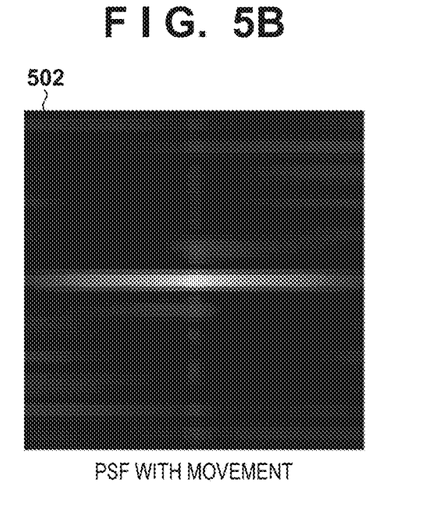

Next, in step S309 and subsequent steps, the image quality evaluation unit 104 determines whether a movement is occurring with the PSF calculated in step S306. A PSF with no occurrence of movement has an impulse shape as shown in 501 of FIG. 5A. On the other hand, a PSF with occurrence of movement has a line shape as shown in 502 of FIG. 5B. This is because the movement was limited to one direction when the detection region was configured locally in step S303. Hence, the occurrence of movement is determined by extracting the feature of the line shape from the PSF.

Figure 6A:
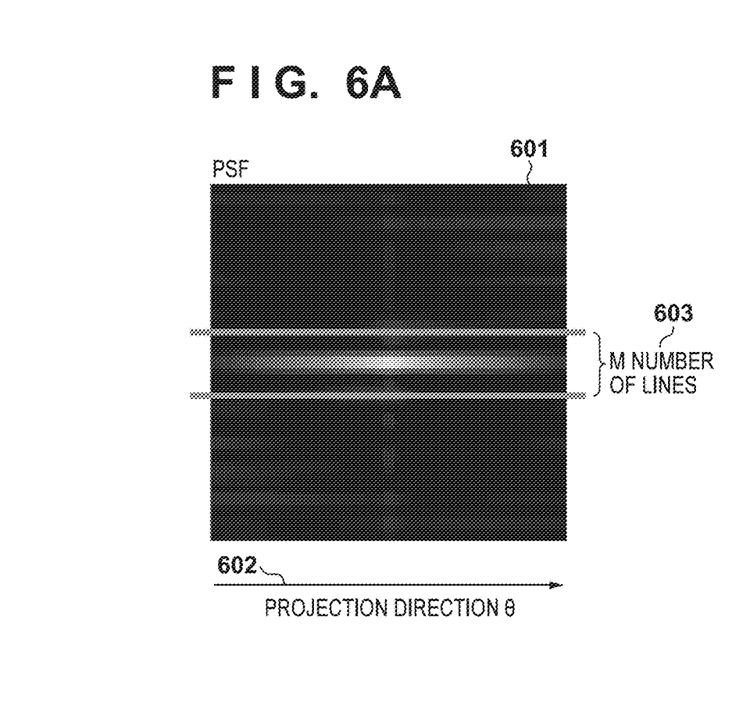
FIGS. 6A and 6B are views each showing a PSF projection.
Figure 6B:
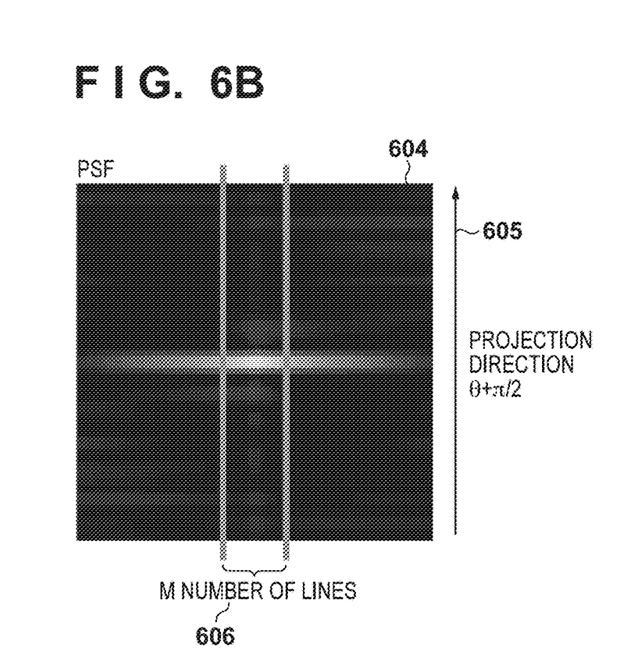

First, as shown in FIGS. 6A and 6B, projection data is acquired from the PSF (step S309). A projection is made in a specific projection direction 602 from a PSF 601 in FIG. 6A. A projection is also made in a projection direction 605 perpendicular to a specific direction from a PSF 604 (the same PSF as the PSF 601) in FIG. 6B. In this manner, projections made from the PSF in two directions which are perpendicular to each other are acquired as a single set of data. The projection data also undergoes projection, as shown in 603 and 606 of the respective FIGS. 6A and 6B, for a line which passes through the center of the PSF and a plurality of lines surrounding the line. For example, when θ=0 in FIGS. 6A and 6B, the projection result is expressed as $$\sum_{j=-m}^{j=m} \sum_{i=-n}^{i=n} h_{ij} \cdot w_{ij} \quad (6)$$

where w represents a weight.

Figure 7A:
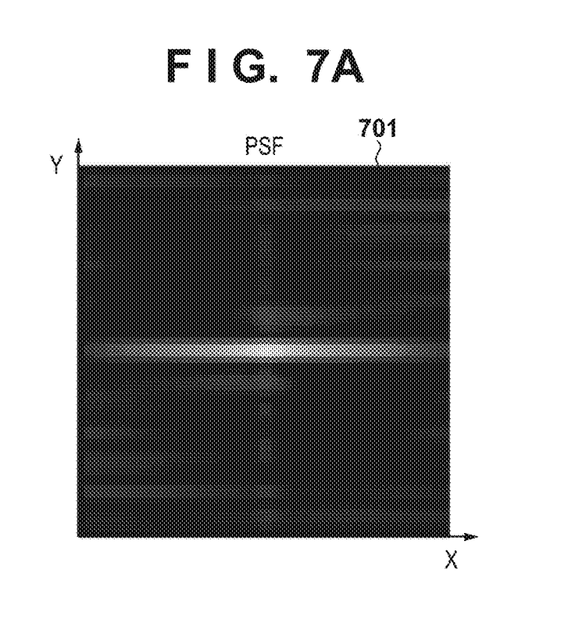
FIGS. 7A and 7B are views each showing a PSF profile.
Figure 7B:
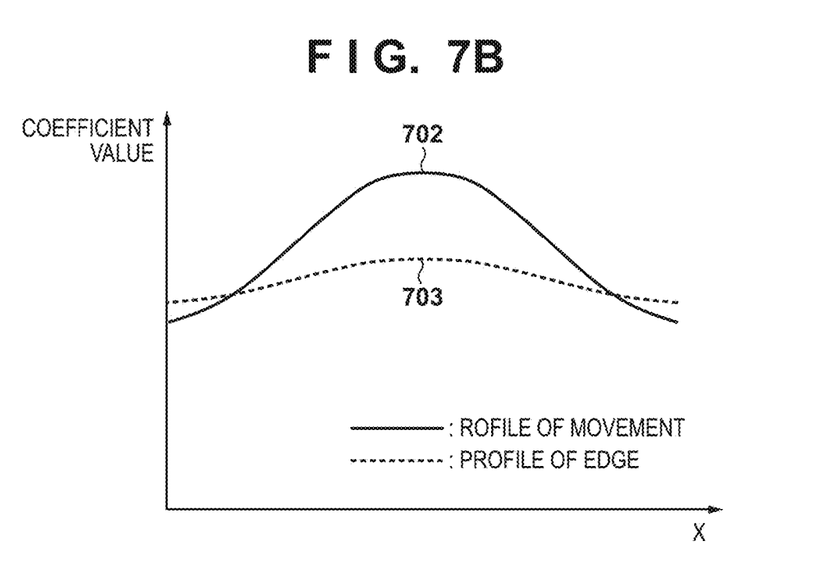

Since the calculated PSF is an approximate solution, it has a shape having a certain degree of spread with respect to an ideal shape. Hence, by also projecting the peripheral plurality of lines, it becomes possible to grasp the features in detail. Preferably, w is a value that increases the weight of a central portion of the PSF. When edge information becomes included in the PSF, it is expressed linearly like a movement. However, due to its length, the edge is often grasped as a larger movement and formed in a manner like the profiles of FIGS. 7A and 7B. When there is a PSF such as 701 in FIG. 7A and a profile is taken in the X-axis direction, in the case of a movement, the shape has a large coefficient value in the central portion as shown in 702 in FIG. 7B. However, in the case of an edge, since it is grasped as a larger movement, the profile spreads more uniformly, and the difference between the coefficient values of the central portion and the edge portions is small. Therefore, by weighting the central portion, a movement and an edge can be distinguished.

A ratio of projected values is calculated (step S310) by letting the larger one of the projected values be the numerator. Since a movement can occur in various directions, sets of a plurality of directions are acquired and the ratios are calculated, respectively (step S311). That is, in step S311, it is determined whether the processes of steps S309 and S310 have been performed for all of the predetermined directions. If the processes have been executed in all of the directions (YES in step S311), the process advances to step S312. Otherwise (NO in step S311), the processes of steps S309 and S310 are executed in each direction in which the processes have not been performed. Since a PSF with no movement has an impulse shape, its ratio is close to 1. In contrast, since a PSF with a movement has a line shape, its ratio becomes larger than 1. The largest value out of the plurality of calculated projection ratios is selected as the representative value, and the selected representative value is compared to a threshold to determine whether a movement is occurring (step S312). Since all blur components are included in the PSF, a blur due to a fluorescent body may appear. Since many of these blurs have no directivity, they appear in a concentric spherical shape in the PSF. Hence, the influence of the blurs will be considerably minimal if projection ratios are taken, and the blurs will not largely influence the movement detection accuracy.

Figure 8:
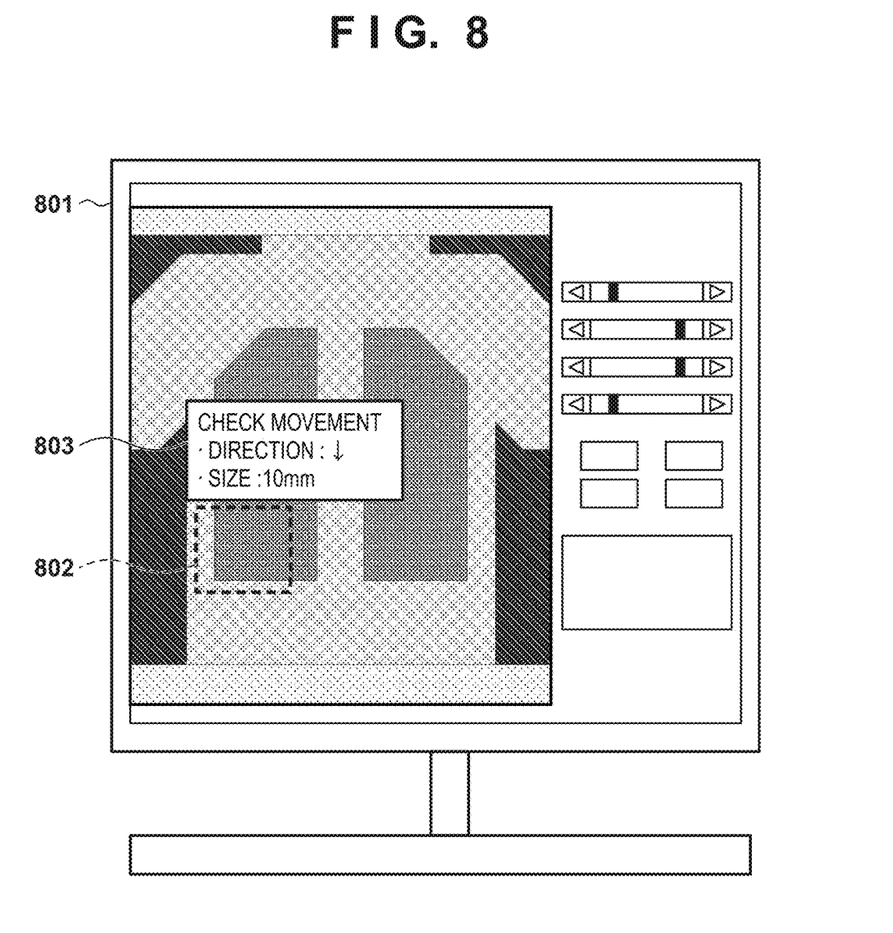
FIG. 8 is a view showing an example of movement detection result display.

Finally, the display unit 105 displays the movement detection result (step S313). As shown in FIG. 8, if a movement is occurring, not only its occurrence but also its location, direction, and the like are displayed on a monitor 801. As the location, the entire region where the movement has been detected may be displayed or a detection region 802 having the highest possibility of the occurrence of the movement may be displayed as a representative region. For example, a region having the largest projection ratio out of the ratios calculated in steps S310 to S312 can be selected and displayed as the detection region having the highest possibility. The movement direction is the direction in which the PSF spreads in a line shape. The direction in which the region calculated as having the largest projection ratio is projected can be used as the movement direction. Together with the detection result, the display unit 105 displays a message 803 that prompts the user to confirm the movement.

As described above, in this embodiment, image quality degradation is associated with an optical image degradation to acquire a point spread function (function acquisition) from a radiation image that has captured an object, and the presence/absence of movement of the object in the radiation image is determined based on the point spread function. More particularly, the presence/absence of movement is determined based on the shape of the point spread function. Hence, the movement of the object can be detected with higher accuracy than a method based on an edge or a response frequency.

In this embodiment, the movement of the object is determined when the point spread function has a line shape. More particularly, the presence/absence of movement of the object is determined based on the ratio of the length obtained from the shape when the point spread function is projected in the first direction and the length when the point spread function is projected in the second direction. Hence, it becomes possible to rapidly detect the absence/presence of movement by simple processing. In addition, when the point spread function is projected, a more central portion of the point spread function is weighted by a larger weighting coefficient, and the point spread function is projected in the first direction and the second direction. This can minimize a detection error due to an edge. Furthermore, since the movement direction is also determined based on the direction of the spread of the point spread function, the movement can be detected in more detail.

In this embodiment, the radiation image is analyzed to configure an acquisition region for acquiring the point spread function in the radiation image, and the point spread function is acquired in this acquisition region. Then, the presence/absence of movement of the object is determined based on the shape of the point spread function acquired in the acquisition region. More particularly, the presence/absence of movement is detected by configuring a region acquired by excluding the collimation region and the direct ray region from the radiation image as the acquisition region and acquiring the point spread function. Hence, the presence/absence of movement can be efficiently detected by executing processing for only the region where the movement may occur.

In this embodiment, the radiation image is divided into a plurality of blocks to configure a block included in the plurality of blocks as the acquisition region, and the point spread function is acquired in each block configured as the acquisition region. The presence/absence of movement of the object is determined, for each block, based on the shape of the acquired point spread function. Hence, according to this embodiment, the detection region can be configured efficiently.

Furthermore, the display unit 105 is caused to display a display indicating the determined presence/absence of movement and the direction of movement (display control). Hence, the user can use the radiation image to effectively make a diagnosis.

In the aforementioned embodiment, an example of the arrangement to configure a region acquired by excluding a collimation region and a direct ray region from the entire radiation image as the PSF detection region has been described. In another embodiment of the present invention, the radiation image is divided into a plurality of blocks, and whether to configure a PSF detection region is determined for each block based on entropy, the signal to noise ratio, the thin-line index, and the like. Hence, according to this embodiment, each detection region necessary to more accurately detect a movement can be configured.

Figure 9:
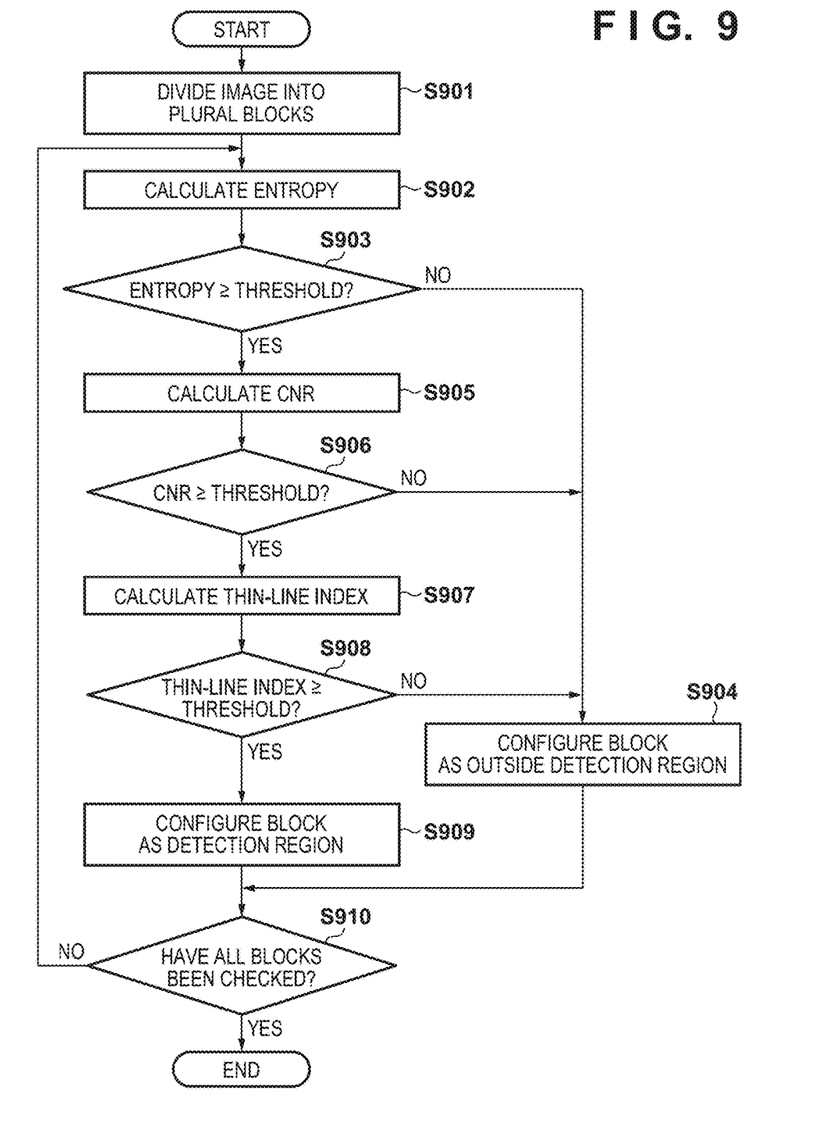
FIG. 9 is a flowchart showing a processing procedure of movement detection region configuration processing.

The other embodiment related to a detection region configuration method will be described in accordance with the procedure of the processing with reference to the block diagram of FIG. 1 and the flowcharts of FIGS. 3 and 9. FIG. 9 is a flowchart showing the detailed procedure of processing to configure the PSF detection region to be executed in step S303 of FIG. 3.

The same processes as those in the aforementioned embodiment are executed in steps S301 and S302. Next, a detection region configuration unit 102 configures a region to calculate the PSF (step S303).

First, the image is divided into a plurality of blocks in the same manner as in the aforementioned embodiment (step S901). The direct ray region is excluded from the detection region for each divided block. Here, an entropy within a block is used to discriminate the direct ray region. An entropy H is calculated (step S902) by $$H = -\sum_{i=0}^{2^K-1} p_i \log_2 p_i \qquad (7)$$

$$p_i = N_i / N$$

where i represents a pixel value, and K represents the number of bits of the image. N represents the total number of pixels, and $N_i$ is the number of pixels of the pixel value i. Hence, $p_i$ represents the occurrence probability of the pixel value i, and the entropy H represents a value expressing the information amount in the region. Since no object is captured in the direct ray region, the region is almost uniform. As a result, the information amount is small, and the value of the entropy H becomes small. The block which has an entropy H equal to or less than a threshold is excluded from the detection region as a direct ray region (steps S903 and S904). That is, in step S903, whether the entropy H is equal to or more than a predetermined threshold is determined. If the entropy H is equal to or more than the threshold (YES in step S903), the process advances to step S905. Otherwise (NO in step S903), the process advances to step S904, and this block is configured outside the detection region.

Next, the CNR (Contrast to Noise Ratio) within the block is calculated (step S905). The PSF is calculated, as an approximate solution, so as to make the error between the PSF and the degraded image small. Hence, information about the state of the structure of the object is necessary. However, if there is much noise, the object information becomes buried in noise. As a result, the error between the noise of the restored image and the noise of the degraded image is calculated to be small, and it is determined that no movement has occurred. Therefore, by calculating the CNR, a block that will not lead to an erroneous determination due to noise in the detection result is selected. For example, C and N are respectively calculated and their ratio (C/N) is set as CNR by $$C = \sum_{j=-k}^{k} \sum_{i=-k}^{k} (\nabla(x_{ROI}(i, j)))^2 \tag{8}$$

$$N = \sqrt{Q_n^2 \cdot (\text{Mean}(x_{ROI}(i, j))/s) + S_n^2} \tag{9}$$

where C represents a square sum of differential values in the block. $Q_n$ represents random quantum noise, $S_n$ represents random system noise, and s represents sensor sensitivity.

Then, whether the calculated CNR value is equal to or more than a predetermined threshold is determined (step S906). Since it is difficult to correctly calculate the PSF in a region having a CNR which is less than the threshold (NO in step S906), this region is excluded from the detection region (step S904). Note that, here, although an example in which the detection region is determined by calculating the CNR has been described, it may be determined by only the noise amount. In this case, since it is difficult to correctly calculate the PSF in a region having a noise amount which is equal to or less than a threshold, this region is excluded from the detection region.

Next, the thin-line index is calculated (step S907). The thin-line index is an index expressing the directivity of a thin line. When a linear object such as an edge is included in the image when the PSF is calculated, this movement may result in an erroneous determination. Hence, it is necessary to exclude, from a detection target region, a block that includes an edge which may lead to an erroneous determination. However, because the object structure is complex, if all of the blocks including an edge are excluded, the number of detection regions become small, and may cause a reduction in the detection accuracy. Therefore, the influence of an edge inside each block is estimated in this embodiment. In this embodiment, since an image quality evaluation unit 104 determines a movement by using a PSF projection ratio, the estimation of edge influence can be performed using a block that will not influence the projection ratio result. The projection ratio is acquired by comparing the projections of directions which are perpendicular to each other. The total sum of the edge components of two perpendicular directions in each block is calculated. If this ratio is close to 1, the influence of the edge on the movement determination is small. Thus, the edge within a block is extracted first. Edge extraction can be performed by using, for example, an edge extraction filter such as the sobel filter or the canny filter. Next, a differential image of a specific direction in the block and a differential image perpendicular to that specific direction are calculated. Subsequently, the sum of the differential images of the specific direction on the edge in the block and the sum of the differential images in the perpendicular direction are calculated to obtain the ratio. When obtaining the ratio, the large value is set as the numerator. This value is set to be the thin-line index.

Next, whether the calculated thin-line index value is equal to or more than a predetermined threshold is determined (step S908). If the thin-line index is less than the threshold (NO in step S908), the edge is determined to have directivity. Since the PSF may not be correctly calculated, this block is excluded from the detection region (step S904). In this manner, even if a PSF cannot be obtained correctly due to an edge, a PSF that is sufficient to determine whether a movement is occurring can be obtained. Since the probability of missing a movement is reduced in accordance with the increase in the number of detection regions for determining a movement, the movement detection accuracy can be improved.

The block that satisfies all of the aforementioned conditions (YES in step S909) is configured as the detection region (step S909). The above-described processing is executed for all of the divided blocks (step S910). Since the same processes as those of the aforementioned embodiment are performed from steps S304 to S313, a detailed description thereof is omitted.

As described above, in this embodiment, the acquisition region in a radiation image is configured based on at least one of the entropy, signal to noise ratio, and thin-line index in the radiation image. Here, the thin-line index is used to evaluate the edge intensity in the radiation image. Hence, according to this embodiment, it is possible to more effectively configure a detection region necessary to accurately detect a movement.

Additionally, in this embodiment, considering that the presence/absence of movement of the object is determined based on the ratio of the lengths of shapes obtained by projecting the point spread function in the respective first and second directions, the acquisition region in the radiation image is configured based on the ratio of the edge intensities in the respective first and second directions in the radiation image. Hence, processing of configuring an acquisition region in the radiation image based on the edge intensity can be effectively performed.

In the aforementioned embodiment, a detection region configuration method that considers the PSF calculation method and the movement determination method has been described. However, if the PSF is calculated in all of the detection regions, the performance cost may become poor. Hence, a maximum detection region count may be configured in accordance with the performance in advance. The detection region configuration unit 102 receives the maximum detection region count and further narrows down the detection regions from the regions configured as the detection regions. For example, the thin-line index calculated for each region is used. The detection regions are sorted in ascending order of thin-line indices and selected from regions in descending order. The possibility of missing a movement becomes higher as the detection region count decrease. However, the smaller the thin-line index, the less the influence of the edge, and the risk of error detection is minimized. In the same manner, the detection regions may be sorted by CNR to determine the regions to calculate the PSF. That is, based on both or one of the thin-line index and the CNR, the priorities of the regions to calculate the PSF are determined, and the PSF can be calculated from the region having the highest priority for the predetermined maximum detection region count.

As described above, in this embodiment, a predetermined number of blocks are configured as the acquisition regions to acquire the point spread functions. To do so, for example, the predetermined number of blocks are configured as the acquisition regions from blocks decided according to the analysis result of the radiation image and have high priority to be configured as the acquisition regions. Hence, it becomes possible to improve the performance of processing while allowing high accuracy movement detection to be performed.

A method of further narrowing down the detection regions from the regions configured as the detection regions by the detection region configuration unit 102 will be described. As a result of the narrowing down the detection regions, if the detection regions are focused in a specific location, the risk of missing a movement becomes high. Hence, the detection regions are distributed evenly in the object. Object extraction may be performed by removing the collimation region and the direct ray region as shown in the aforementioned embodiment or using machine learning. Then the extracted object is divided into a plurality of areas. The division can be performed by, for example, simply equally dividing the object. Alternatively, a result obtained from clustering using the k-means method or the like may be used. The detection regions are sorted and selected, out of the divided regions, using the thin-line indices and the CNR values in the manner of the aforementioned embodiment, and a movement can be detected whatever the portion of the image that it occurs in.

The X-ray exposure time can be controlled by the imaging procedure. When the exposure time becomes long, the distance moved by the movement becomes long accordingly. In general, if the moving distance becomes long, the detection accuracy of image quality degradation due to movement is reduced. Hence, the exposure time is input to the detection region configuration unit 102, and the size of each detection region is changed depending on the exposure time. If the movement is moving at a constant speed, the amount of movement increases in accordance with the amount of increase of the exposure time. Therefore, the region is configured to spread as much as the amount of this increase. Let T[msec] be the reference exposure time and M×N be the detection region size at that time. A detection region size M'×N' when the exposure time is changed to T'[msec] is changed as $$M' = \frac{T'}{T} \cdot M, N' = \frac{T'}{T} \cdot N \tag{10}$$

Since the moving distance decreases in accordance with the amount of decrease of the exposure time, the detection region size need not be changed. Since the PSF cannot be calculated if the exposure time becomes long and M' and N' exceed a predetermined size, a message notifying the user that the movement cannot be detected is displayed by the display unit 105.

In the above-described manner, in this embodiment, a wider acquisition region is configured and the movement is detected based on this wider acquisition region in accordance with radiation exposure being performed for a long time upon capturing a radiation image. Hence, according to this embodiment, even if a large movement occurs when radiation exposure is performed for a long period of time, the presence/absence of movement can be detected with high accuracy.

The X-ray exposure time can be controlled by an imaging technique. In the aforementioned embodiment, considering that the moving distance becomes long in accordance with the movement, the example of an arrangement that increases the detection region size has been described. In this embodiment, the presence/absence of movement is accurately detected by increasing the PSF size even if the exposure time becomes long.

As described in the aforementioned embodiment, the PSF size is decided in accordance with the amount of detected movement. Since there is a tendency for the amount of detected movement to increase in accordance with the increase in exposure time, the detection accuracy can be held by changing the PSF size. The exposure time is input to a function calculation unit 103, and the PSF size is changed by the exposure time. Let T[msec] be the reference exposure time and $P_M \times P_N$ be the PSF size at the time. The size $P_M' \times P_N'$ of the PSF when the exposure time changes to T[msec]' is changed as $$P'_M = \frac{T'}{T} \cdot P_M, P'_N = \frac{T'}{T} \cdot P_N \tag{11}$$

Since the moving distance decreases in accordance with the amount of decrease of the exposure time, the PSF size need not be changed. Since the PSF cannot be calculated if the exposure time becomes long and $P_M'$ and $P_N'$ exceed the detection region size, a message notifying the user that the movement cannot be detected is displayed by the display unit 105.

As described above, in this embodiment, a larger point spread function is acquired and a movement is detected in accordance with radiation exposure being performed for a long time upon capturing a radiation image. Hence, even if radiation exposure is performed for a long time and a large movement occurs, the presence/absence of movement can be detected with high accuracy.

In each embodiment of the present invention, in the X-ray image processing apparatus that detects image degradation of a radiation image, a restored image and a point spread function are calculated from the degraded radiation image, and image degradation is evaluated based on this point spread function. Hence, a movement can be detected regardless of the type of movement and the image structure, and the movement detection accuracy can be improved. As a result, the work efficiency of a technician improves, and the burden on the patient is also reduced.

According to the present invention, a technique of automatically detecting, with higher accuracy, the image quality degradation due to movement can be provided.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™, a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-200473, filed on Oct. 8, 2015, which is hereby incorporated by reference herein in its entirety.

What is claimed is:

1. An image processing apparatus comprising:
one or more processors; and
a memory storing a program which, when executed by the one or more processors, causes the one or more processors to function as units comprising:
(1) an image acquisition unit adapted to acquire a radiation image capturing an object;
(2) a function acquisition unit adapted to acquire a point spread function from the radiation image; and
(3) a determination unit adapted to determine, based on a ratio of a length of a shape based on the point spread function projected in a first direction and a length of a shape based on the point spread function projected in a second direction, presence/absence of a movement of the object.

2. The apparatus according to claim 1, wherein the function acquisition unit acquires the point spread function from the radiation image by repeating processing that acquires, based on a first restored image of the radiation image, a first point spread function, and the radiation image, a second restored image as the updated first restored image and acquires, based on the second restored image, the first point spread function, and the radiation image, a second point spread function as the updated first point spread function, until a difference between the radiation image and an image acquired by applying the second point spread function to the second restored image becomes less than a predetermined value.

3. The apparatus according to claim 1, wherein the program causes the one or more processors to further function as a display control unit adapted to cause a display unit to display the presence/absence of the movement determined by the determination unit.

4. The apparatus according to claim 1, wherein the determination unit determines, based on a shape of the point spread function, the presence/absence of the movement of the object.

5. The apparatus according to claim 4, wherein the determination unit determines, when the point spread function has a line shape, the presence of the movement of the object.

6. The apparatus according to claim 5, wherein the determination unit determines, based on the first direction and the second direction in which the point spread function spreads, a direction of the movement.

7. The apparatus according to claim 1, wherein the determination unit projects, by weighting a larger weighting coefficient on a more central portion of the point spread function, the point spread function in the first direction and in the second direction.

8. The apparatus according to claim 1, wherein the program causes the one or more processors to further function as a configuration unit adapted to configure, by analyzing the radiation image, an acquisition region to acquire a point spread function in the radiation image,
wherein the function acquisition unit acquires the point spread function in the acquisition region, and
wherein the determination unit determines, based on a shape of the point spread function acquired in the acquisition region, the presence/absence of the movement of the object.

9. The apparatus according to claim 8, wherein the configuration unit divides the radiation image into a plurality of blocks and configures a block included in the plurality of blocks as the acquisition region,
wherein the function acquisition unit acquires a point spread function in each block configured as the acquisition region, and
wherein the determination unit determines, based on a shape of the acquired point spread function, the presence/absence of the movement of the object for each block.

10. The apparatus according to claim 9, wherein the configuration unit configures each of a predetermined number of blocks as the acquisition region.

11. A control method of an image processing apparatus, the method comprising:
acquiring, by an image acquisition unit, a radiation image capturing an object;
acquiring, by a function acquisition unit, a point spread function from the radiation image; and
determining, by a determination unit, based on a ratio of a length of a shape based on the point spread function projected in a first direction and a length of a shape based on the point spread function projected in a second direction, presence/absence of a movement of the object.

12. A non-transitory computer-readable storage medium storing a computer program for causing a computer to function as each unit of an image processing apparatus, the apparatus comprising:
an image acquisition unit adapted to acquire a radiation image capturing an object;
a function acquisition unit adapted to acquire a point spread function from the radiation image; and
a determination unit adapted to determine, based on a ratio of a length of a shape based on the point spread function projected in a first direction and a length of a shape based on the point spread function projected in a second direction, presence/absence of a movement of the object.

* * * * *